US00PP15032P2

(12) United States Plant Patent
Westhoff

(10) Patent No.: US PP15,032 P2
(45) Date of Patent: Jul. 27, 2004

(54) LOBELLA PLANT NAMED 'LOBETO'

(50) Latin Name: *Lobelia erinus*
Varietal Denomination: Lobeto

(75) Inventor: Heinrich Westhoff, Oeding (DE)

(73) Assignee: Syngenta Seeds B.V., Enkhuizen (NL)

( * ) Notice: Subject to any disclaimer, the term of this patent is extended or adjusted under 35 U.S.C. 154(b) by 49 days.

(21) Appl. No.: 10/342,714

(22) Filed: Jan. 15, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—Bruce Vrana; Edouard G. Lebel

(57) ABSTRACT

A new Lobelia plant particularly distinguished by its trailing plant habit, large flower size and an intensive flower color.

1 Drawing Sheet

Latin name of the genus and species of the plant claimed: *Lobelia erinus.*
Varietal denomination: 'Lobeto'.

BACKGROUND OF THE NEW PLANT

The present invention relates to a new and distinct cultivar of Lobelia plant, botantially known as *Lobelia erinus.* The new cultivar is propagated by cuttings resulting from the cross between female parent, *Lobelia erinus* 'Wesstar' (U.S. Plant Pat. No. PP12,678), and male parent, wild white Lobelia (unpatented).

As a result of this cross, the present cultivar was created in 1998 in Sudlohn-Oeding, Germany and has been repeatably asexually reproduced by cuttings in Enkhuizen, Netherlands over a two-year period. It has been found to retain its distinctive characteristics through successive propagations, and this novelty appears to be firmly fixed.

DESCRIPTION OF THE DRAWING

This new Lobelia plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new Lobelia plant. The data which defines these characteristics were collected from asexual reproductions carried out in Enkhuizen, Netherlands. The plant history was taken on 12 weeks old plants. Color references are primarily to The R.H.S. Colour Chart of The Royal Horticultural Society of London.

Comparison Between the New Cultivar 'Lobeto' and a Similar Cultivar

| | 'Lobeto' | 'Blue Star' (unpatented) |
|---|---|---|
| Plant height | 12 cm | 10 cm |
| Plant width | 35 cm | 35 cm |

-continued

| | 'Lobeto' | 'Blue Star' (unpatented) |
|---|---|---|
| Plant shape | Trailing | Spreading |
| Flower color | | |
| Upper surface | 99B | 95B |
| Lower surface | 97A | 100A |
| Flower tube | 95C | 95C |

The plant:
*Classification.*—Botanical *Lobelia erinus.*
Parentage:
*Female parent.*—*Lobelia erinus* 'Wesstar' (U.S. Plant Pat. No. PP12,678), bred in 1996.
*Male parent.*—Wild white Lobelia (unpatented).

Comparison Between *Lobelia erinus* 'Lobeto' and its Female Parent

| *Lobelia erinus* 'Lobeto' | *Lobelia erinus* 'Wesstar' |
|---|---|
| Plant shape is more trailing | Plant shape is more spreading |
| Flower color RHS 099B | Flower color RHS 095 B–C |
| Leaves are bigger | Leaves are smaller |
| Sepals are smaller | Sepals are bigger |

Comparison Between *Lobelia erinus* 'Lobeta' and its Male Parent

| *Lobelia erinus* 'Labeto' | Wild white Lobelia |
|---|---|
| Leaves are darker green | Leaves are lighter green |
| Flower color is blue | Flower color is white |

Plant description:
*Growth habit.*—Trailing.
*Plant height.*—12 cm.
*Speading area of plant.*—35 cm.
*Growth rate.*—Moderate growth.
*Strength.*—Good.

*Branching character.*—Freely branching and lateral branching at every node. Pinching will enhance branching. Branches strong and flexible.

*Blooming period.*—From May until October.

The stem:

*Diameter.*—15 mm.

*Texture.*—Smooth, slightly pubescent, glossy.

*Color.*—RHS 147A.

*Length of internode.*—15 mm, depending on the light conditions where the plant is propagated.

*Shape.*—(Tri)angular.

The foliage:

*Shape.*—Leaves simple, generally symmetrical and flat. Broadly ovate with rounded apex, obtuse to attenuate base and crenate margin.

*Texture.*—Slightly pubescent, glossy.

*Length.*—Young 36 mm, fully expanded 54 mm.

*Width.*—Young 10 mm, fully expanded 24 mm.

*Color.*—Upper side RHS 147A. Lower side RHS 79B.

The flower:

*Type and habit.*—Flowers form at apical axils, usually one flower per axil. Flowers labiate, upper lip consisting of two small petals and lower lip consisting of three larger and broader petals. Petals are fused at base into a tube. Freely and continuously flowering. Flowers face outward. Flowers persistent. Texture, slightly pubescent. Oblong shape with acute apex and entire margin.

*Flower.*—Width upper petals 2 mm, lower petals 6 mm. Length upper petals 5 mm, lower petals 11 mm. Depth 7 mm.

*Texture.*—Smooth, pubescent.

*Buds.*—Length 10 mm. Diameter 3 mm. Form Tubular. Color Light green.

*Flower color.*—Upper surface RHS 99B. Lower surface RHS 97A. Flower tube RHS 95C.

*Sepals.*—No. of sepals 5. Length 6 mm. Width 0.5 mm. Texture Smooth, slightly pubescent. Color RHS 147B.

*Flower stem.*—Length 23 mm. Angle Upright. Strength Rigid, flexible. Color RHS 147A.

*Flower throat.*—Color Upper RHS 97A. Lower RHS 97A, spots RHS 99A. Texture Whiskered.

Reproductive organs:

*Androecium.* Stamen number 5. Anther shape Oblong. Anther length 2 mm. Pollen color RHS 202B. Amount of pollen Moderate.

*Gynoecium.*—Pistil length 10 mm. Stigma shape Bilobate. Stigma diameter 1 mm. Stigma color N87A. Style color Light green. Ovary color RHS 147A.

The fruit:

*Fruit size.*—Diameter 2 mm.

*Fruit length.*—5 mm.

*Fruit color.*—RHS 147A.

Seed development:

*Some seed development has been observed on plants of the new Lobelia.*—Seed colour Brown. Seed shape Round.

Disease resistance: No susceptibility or resistance to fungal, bacterial or viral pathogens has been noted.

What is claimed is:

1. A new and distinct variety of Lobelia plant, substantially as illustrated and described herein.

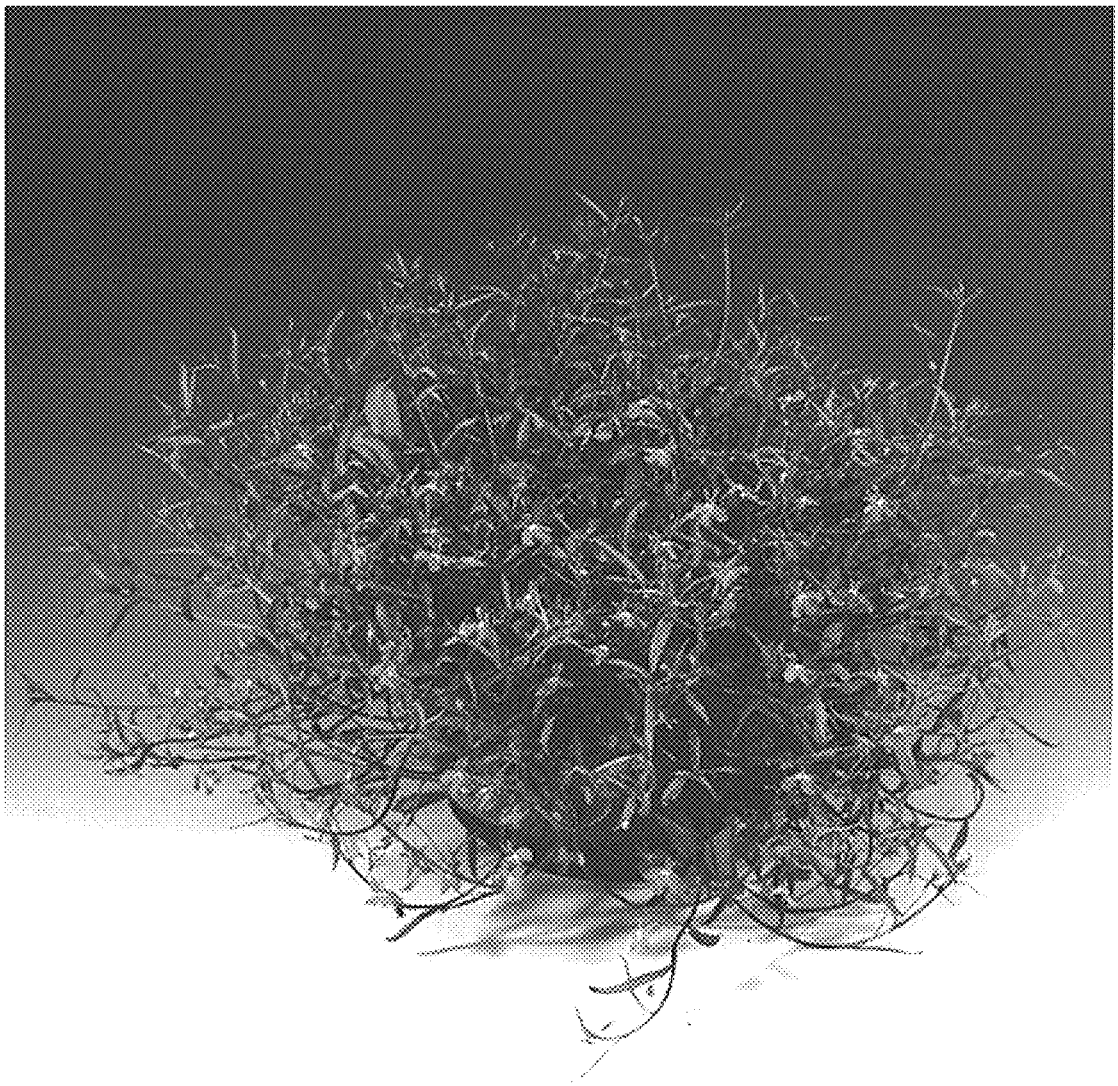

* * * * *